(12) United States Patent
Gundersen

(10) Patent No.: US 9,185,961 B2
(45) Date of Patent: Nov. 17, 2015

(54) SOFT EDGE PAD

(75) Inventor: Dag H. Gundersen, Tolvsrød (NO)

(73) Assignee: Padtech AS, Snaroeya (NO)

( * ) Notice: Subject to any disclaimer, the term of this patent is extended or adjusted under 35 U.S.C. 154(b) by 1029 days.

(21) Appl. No.: 13/203,981

(22) PCT Filed: Mar. 2, 2010

(86) PCT No.: PCT/NO2010/000082
§ 371 (c)(1),
(2), (4) Date: Nov. 16, 2011

(87) PCT Pub. No.: WO2010/101474
PCT Pub. Date: Sep. 10, 2010

(65) Prior Publication Data
US 2012/0051828 A1    Mar. 1, 2012

(30) Foreign Application Priority Data
Mar. 3, 2009 (NO) .................................. 20090967

(51) Int. Cl.
*A45D 37/00* (2006.01)
*A61F 13/00* (2006.01)

(52) U.S. Cl.
CPC ............... *A45D 37/00* (2013.01); *A61F 13/00* (2013.01); *A45D 2200/1018* (2013.01); *A45D 2200/1036* (2013.01); *A45D 2200/1045* (2013.01); *A61F 2013/0017* (2013.01); *A61F 2013/00297* (2013.01)

(58) Field of Classification Search
CPC ........... A45D 37/00; A45D 2200/1009; A45D 2200/1018; A45D 2200/1036; A45D 2200/1045
USPC .............................................. 401/7, 196, 261
See application file for complete search history.

(56) References Cited

U.S. PATENT DOCUMENTS

| 3,082,468 | A | * | 3/1963 | Wattles | A45D 37/00 |
| | | | | | 15/104.94 |
| 3,124,825 | A | | 3/1964 | Iovenko | |
| 3,806,260 | A | * | 4/1974 | Miller | A47L 23/10 |
| | | | | | 15/104.94 |
| 4,603,069 | A | * | 7/1986 | Haq | A45D 37/00 |
| | | | | | 15/104.001 |
| 4,832,942 | A | * | 5/1989 | Crace | A61B 19/36 |
| | | | | | 15/244.3 |

(Continued)

FOREIGN PATENT DOCUMENTS

| CN | 2475670 | 2/2002 |
| FR | 2492776 Y | 4/1982 |

(Continued)

OTHER PUBLICATIONS

Translation of CN office action of Apr. 3, 2013.

*Primary Examiner* — David Walczak
*Assistant Examiner* — Bradley Oliver
(74) *Attorney, Agent, or Firm* — Christian Abel

(57) ABSTRACT

The present invention relates to a device for applying at least one product at a de-sired place or spot. The device comprises several layers, where an impermeable top layer (1) and an impermeable bottom layer (4) will form the outer surfaces of the device, between which two outer surfaces a storage layer (3) and a contact layer (2) are arranged. The bottom layer (4), storage layer and contact layer (2) are welded together inside their edges to form a closed storage chamber (10) for the product and further being connected (6) around their common edges, where at least a part of the bottom layer (4) outside and around the closed storage chamber (10) is cut away, in order to create a device with soft edges.

9 Claims, 3 Drawing Sheets

(56) References Cited

U.S. PATENT DOCUMENTS

| | | | |
|---|---|---|---|
| 5,961,500 A | 10/1999 | Weinstein | |
| 6,494,767 B2 * | 12/2002 | Fisher | A47L 13/19 15/104.94 |
| 8,403,582 B2 * | 3/2013 | Bischoff | A47L 13/17 401/132 |
| 2005/0284777 A1 | 12/2005 | Wilkman | |
| 2006/0163101 A1 | 7/2006 | Pauchet | |
| 2007/0048062 A1 * | 3/2007 | Brunner et al. | 401/7 |
| 2011/0232565 A1 * | 9/2011 | Gundersen | A47L 13/17 118/264 |
| 2012/0059339 A1 * | 3/2012 | Gundersen | A45D 34/04 604/304 |
| 2014/0208532 A1 * | 7/2014 | Gundersen | A61M 35/006 15/104.93 |
| 2014/0369737 A1 * | 12/2014 | Gundersen | A45D 37/00 401/132 |

FOREIGN PATENT DOCUMENTS

| | | |
|---|---|---|
| FR | 2848535 Y | 6/2004 |
| WO | WO 03/000106 A | 1/2003 |
| WO | WO 2009/009651 Y | 1/2009 |

* cited by examiner

SOFT EDGE PAD

The present invention relates to a device for applying at least one product at a de-sired place or spot. More particular the present invention relates to a pad accommodating at least one product, where the pad comprises several layers that are joined together in appropriate ways, each layer having its own specific function.

There are today different methods available for applying various liquids or colloidal substances, hereinafter referred to as a product, on a desired spot or surface. The product can for instance be applied to a surface by the user simply placing the product from a bottle or tube on their hand and then manually spread on the desired surface. This method is the most inexpensive, but it is also inefficient, messy and may result in an uneven application of the product. Furthermore, the bottles or tubes contain a fairly large quantity of the product and can therefore be inconvenient to carry with the user.

One other method is to have separate bottles and applicator elements. The applicator element will soak up some of the product when they are brought into contact with each other, whereby the user uses the applicator element to disperse the product over a desired spot or surface. This method may result in spillage when applying the product to the applicator element, and some of the product may also be wasted as the applicator element itself will absorb some of the product. A further problem with this method is that the product to be applied may come in contact with the user's hands, which is not desirable, especially if the product is irritating for the skin.

Yet another method for applying a product on a desired surface is to use a disposable or single-use applicator which is supplied with a pre-determined quantity of the product. Such applicators are manufactured from a disposable material substantially fully infused with the appropriate product, for example, a cleansing cream, and sealed in a container. This results in relatively costly manufacture, since a larger amount of the cosmetic product than is required is applied to the sheet of material. The applicator may also be so infused with the product to be applied that it will result in uneven application of the product on the desired surface. It will also be very difficult to control the amount of product transferred from the applicator to the skin, increasing the chance of excessive application of the product.

The above mentioned product can for instance be a liquid, such as wound cleansing agent, special cleansing liquid for various purposes such as, nail varnish, varnish remnants, glue remnants etc. and the colloidal substances can for instance be shoe cream, cosmetics, moisture creams, cleansing creams, self-tanning creams, various gel products for personal hygiene, soap etc. Furthermore, the product can be pharmaceutical products, such as pain relief, anti-itching agents etc.

U.S. Pat. No. 3,124,825 describes a nail polish remover, where there is provided a single use, disposable package including a container drawing positioned therebetween an applicator with enough polish remover impregnated therein to remove the polish from all the nails of a user. The package consists of a flexible pouch heat sealed at its free edges to form an envelope which seals material contained therein from contact with liquids or gases. Within the pouch is an applicator saturated with the nail polish remover.

U.S. Pat. No. 5,961,500 describes a prewetted medical wipe with impermeable barrier, where the wipe is constructed by bonding a layer of absorbent material to one side of a barrier sheet that is impermeable to infectious agents and insoluble in dermatological fluids, filling a reservoir in the barrier with a dermatological fluid, and hermetically sealing the absorbent layer between the barrier and a cover. The peripheral edges of the absorbent layer are spaced inwardly from the peripheral edges of the barrier to provide a surrounding zone of the impermeable barrier alone. The absorbent layer bond to the barrier is resistant to degradation caused by exposure to the dermatological fluid.

A common feature of the applicators shown in the prior art is that they are neither economical nor able to control the application of a product onto a surface.

Many of the known applicators will also have a tendency to leak and/or to desiccate after that the applicator has been stored for a while. Due to this, the applicators are often manufactured from materials that are relatively thick and stiff, which may cause in an irritation, a rash etc. on the surface that is applied the product, especially if the surface is sensitive, for instance if the applicator is used to apply the product on a human skin.

It is therefore an object of the present invention to provide a device which one hand will not leak and/or desiccate during the transportation and storage of the device, and on the other hand will be soft enough to prevent irritation and/or damage on a surface when the device is used.

It is further an object of the present invention to provide an economical device for containing and dispensing a liquid or substance in a convenient, uniform and simple manner to a surface.

It is further an object of the present invention to provide a device which is economical and simple to manufacture.

Still an object of the present invention is to provide a device which will not soil the user during the use of the device.

These objectives are achieved with a device for applying a product onto a surface according to the invention as defined in the enclosed independent claim, where embodiments of the invention are given in independent claims.

According to the present invention it is provided a device that can apply a liquid and/or a colloidal substance in a controlled manner onto a surface or a spot, where the device comprises several layers that are jointed in appropriate ways in order to create a liquid tight device. Each of the layers of the device has its own specific function.

A typical device according to the present invention may for example consist of five different main layers, where a top layer and a bottom layer will form the outer surfaces of the device, thereby sealing off the device.

According to one preferred embodiment of the present invention, the device is comprised of a top layer, a contact layer, a storage layer a bottom layer that are connected to each other in appropriate ways. An additional pocket layer may be joined to the bottom layer, thereby forming a pocket in the device.

The bottom layer constitutes the rear surface of the device, and serves to protect the storage layer from desiccation, and will also prevent the user from being soiled during use. In a preferred embodiment the bottom layer may also be manufactured as a pocket (comprising an additional outer elastic layer) or comprise a holding device, in order to ease the use of the device. The bottom layer may be manufactured from a liquid-impermeable material, for instance a plastic film that has good welding properties, in order to be attached to the one or more of the other layers. The attachment between the different layer(s) may for instance be done by means of a heat-seal, ultrasonic weld or adhesive to prevent its removal from the other layer(s).

The storage layer according to the present invention may be provided by a fibre structure with intersecting fibres, where the fibres can be situated in one or several layers. The structure of the fibres will form cavities of a size and shape that enable it to contain the specific product that has to be stored.

The size of the cavities may be varied depending on the viscosity of the product to be contained. As the structure substantially is not absorbent, it has to be dosed with or be supplied in another way with a product it has to contain.

The storage structure may also be manufactured from a material having a different cell structure, for instance a rubber sponge material or a non-woven material, having sufficient porosity to store the product to be applied.

The storage layer, due to the properties of the material used, will preferably have a "springy effect", where this will result in that the storage layer releasing some of the product each time the device is compressed. When the pressure on the device is relieved, the remaining product will remain in the storage layer.

The cavities in the storage material may also be made artificial, as one for instance can use a needle, knife or the like, in order to form perforations and/or openings in the storage layer. This is important when a certain amount of a product is to be stored on a specific location in the pad.

According to the present invention, the storage layer may also be manufactured as a multi chambered layer, where this for instance is advantageous when the storage layer contains two or more different products with different density and/or that the products are not to be mixed before the device is to be used. This "chambering" may be achieved by a weakened welding forming a barrier between the chambers, where this barrier will burst or open when a certain pressure is applied to the device.

The contact layer, which is the layer that is in contact with the surface on which the product is to be applied, can be a film or a fabric (e.g. non-woven). The layer has a suitable surface that is selected according to the application for which the device is to be used. If the device, for instance, is to be used as a shoe cream applicator, then the contact layer will have a surface that is suited for spreading out and polishing the shoe when the shoe cream is applied. If, for instance, the device is to be used to cleanse skin with sterile cleansing liquid, the contact layer may also have a surface that is soft against the skin and preferably have a desired degree of roughness to enable it to remove dirt etc. from the user's skin. In such cases the material must often be sterile before use and may therefore be protected by a separate layer that is torn off before use of the device.

The different layers in the device are connected or attached together in appropriate ways. In one embodiment of the present invention the pocket layer, the storage layer, the contact layer and a top layer may be attached to each other, for instance by a weld seam, both inside and around their outer edges, thereby forming a sealed storage chamber in the device.

The above construction of the device will result in that dust, bacteria, moisture, dirt etc. can contaminate the surface of the one or more of the layers, as the different layers are not connected to each other outside the weld seam that forms the sealed storage chamber. In order to prevent this contamination, the different layers are connected to each other also around their edges. This will form a device that is "closed" around its outer edges. However, as the pocket layer is manufactured to be a bit shorter than the other layers, one part of the pocket layer will not be connected to the rest of the layers, whereby this will form the pocket opening in the device. This outer connection can be a simple "weld" or a fluid tight "weld".

The top layer may be manufactured from a plastic film or any other suitable material. In order to ease the tearing-off of the top layer, the top layer may be manufactured with a flap or corner.

When the top layer is removed by tearing, the device is ready for use. The product(s) stored in the storage chamber will remain in the storage chamber until the device is subjected to a mechanical pressure.

The pocket layer is preferably manufactured from an elastic material, but it may also consist of a more stiff material.

According to the present invention a part of at least the bottom layer is cut off or out during the manufacturing of the device, where the cut is done outside and around an area that is to form the sealed storage chamber. This will give a device with soft edges, when the different layers of the device are connected in appropriate ways.

It should be understood that one or more of the other layers of the device can be manufactured in the same way, in order to obtain the desired soft edged device.

The different layers may also be cut, where the cut(s) is/are made from the outer edges of the layers and towards the area that is to form the sealed storage chamber.

It is also possible to manufacture a layer where a part of the layer is cut off or out, where this is combined with one or more cuts made in the layer.

Alternatively the layers may be designed either as layers with only cuts out or layers with only cuts, where the different layers, when arranged adjacent each other, will give the desired soft edged device.

In a preferred embodiment of the device according to the present invention, an additional layer is arranged either between the bottom layer and storage layer or between the bottom layer and the pocket layer. This will prevent the users hand being soiled, even though the product that is contained in the device will be able to flow over or through the sealed storage chamber, as the additional layer is manufactured from a substantially impermeable material.

The additional layer may also be integrated to be a part of the storage layer, or it can alternatively be a part of the bottom layer.

Furthermore, the additional layer must not necessarily be a complete layer (i.e. covering the entire device), it can for example be a half of an ordinary layer.

It should be understood that the device can comprise further additional layers.

Since at least one layer (preferably the stiffer bottom layer) is cut or a part of it is cut off, the device will have a tendency to form an upstanding edge in the area that is cut out when the user puts his or hers finger(s) in the pocket.

The foregoing and other objects, features and advantages of the invention will be apparent from the following more particular description of preferred non-limiting embodiments of the invention, as illustrated in the accompanying drawings:

FIG. 1 shows the principal configuration of a device according to the present invention. As can be seen, the device is comprised of five different layers 1-5, where each layer has its own specific function.

Figure 1:
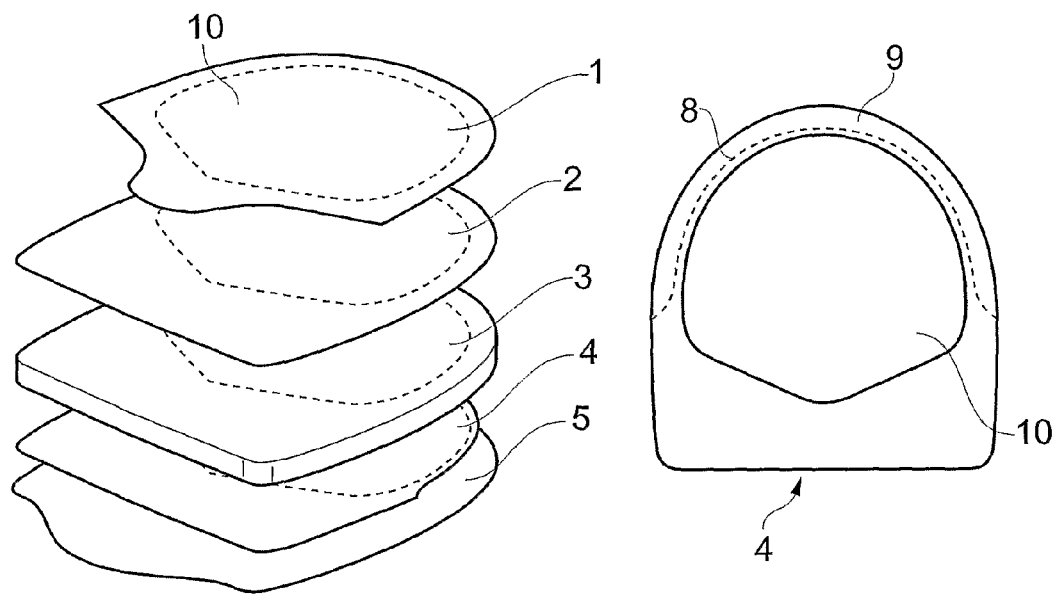
FIG. 1 illustrates a principal configuration of a device according to the present invention.

A substantially impermeable bottom layer 4 and a top layer 1 will form the outer, sealing surfaces of the device. Between these two layers a storage layer 3 and a contact layer 2 are arranged.

As the bottom layer 4 and the top layer 1 are manufactured from materials that are thicker and less flexible than the rest of the layers 2, 3, 5, the device will have relative stiff and sharp edges, which is not desirable if the device is to be used to apply a product to part of the body.

It is therefore desirable to manufacture a device with soft edges, where this is achieved by cutting away at least a part of the bottom layer 4.

The bottom layer 4 must prevent the stored product passing through it and is therefore made from a liquid-impermeable material. On its backside, that is the side turning away from a storing layer 3, the pocket layer 4 is joined with an additional top layer 5, where these two layers 4, 5 will form a pocket in the finished device. The layers in the device are then in appropriate ways "welded" around their outer peripheries, leaving only a certain part of the pocket layer un-welded, thereby forming an opening for the user. The user can then put his or her hand into the pocket when the device is to be used. This pocket will ease the handling of the device and it will also prevent the user getting soiled. This outer joining will also act as an extra security for the prevention of contamination.

The pocket layer 5 is manufactured from an elastic material.

In a further embodiment of the present invention, the top layer 5 may be replaced with a holding device (not shown), for instance a handle or grip device.

Above the bottom layer 4 a three-dimensional storage layer 3 is arranged. The storage layer 3 contains the liquid and/or colloidal substance that is to be applied onto a desired surface or spot, where the product can either be supplied to the storage layer 3 before the different layers 1-4 are connected together or it can be supplied after that the different layers 1-4 have been connected.

The product that is to be contained in the storage layer 3 can for instance be supplied by different kinds of nozzles or needles etc.

Over the storage layer 3 a contact layer 2 is arranged, where this contact layer 2 will allow the product(s) to pass through the contact layer 2 from the storage layer 3 and to the surface on which the product(s) is to be applied. The structure of the contact layer 2 is adapted to the specific product(s) that is to be accommodated in the device, and a side of the contact layer 2 that is facing the surface that is to be applied the product(s) is such that it will disperse the product(s) evenly and sparsely onto the desired surface or spot.

The device according to present invention also comprises a top layer 1, where the top layer 1 is manufactured from a substantially impermeable material. The top layer 1 will, together with the pocket layer 4, form an outer "sealing" of the device. The top layer 1 will also protect the contact layer 2 from fouling.

The top layer 1 must be removed before the device is used, where this can be done by tearing of the top layer 1.

On the right side in FIG. 1 the bottom layer 4 can be seen, where a stippled line 8 indicates how the bottom layer 4 is cut in order to obtain a soft edged device.

Figure 2:
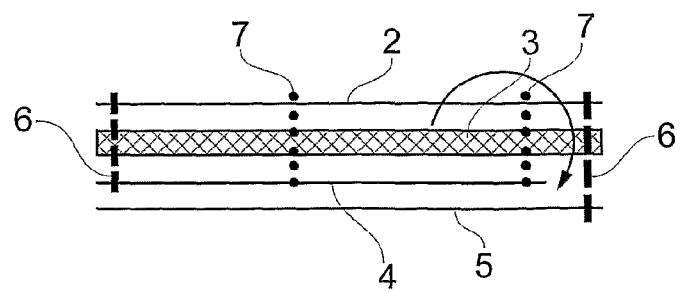
FIG. 2 shows a cross section of the device in FIG. 1.

In FIG. 2 is shown one first embodiment of the present invention.

A cut is performed in the bottom layer 4, where the cut will follow the stippled line 8 (see also FIG. 1), such that a part 9 of the bottom layer 4 is removed. Thereafter the bottom layer 4, the storage layer 3 and the contact layer 2 are placed over each other and connected to each other by a "weld" 7, the "weld" 7 being such that it forms a closed storage chamber 10 in the layers 2-4. The shape of the bottom layer 4 will determine how the "weld" is arranged, as the "weld" must extend to the inside of the edges of the different layers.

The "welding" 7 between the layers 2-4 can be done by means of heat-seal, ultrasonic weld or adhesive etc.

Furthermore, the sealed storage chamber can be made to form several closed compartments in the bottom layer 4, the storage layer 3, the contact layer 2 and the top layer 1. This is desirable when the device is to contain more than one product.

When the layers 2-4 have been connected as described above, a nozzle or needle (not shown) is used to fill the product inside the storage chamber 10. The needle or nozzle can then either inject the fluid directly into the storage chamber 10, the needle or nozzle being brought into the storage layer 3, or deliver the product onto a surface of the contact layer 2, the needle or nozzle being in contact with the surface of the contact layer 2 or being placed at a distance above the contact layer 2.

When the storage chamber 10 has been filled with the product, a top layer 1 is arranged over the contact layer 2 and a pocket layer 5 is arranged on a side of the bottom layer 4 that is facing away from the storage layer 3. The layers 1-5 are then connected 6 around their outer peripheries, in order to form a "sealed" construction. As can be seen in FIG. 2, the right side of the bottom layer 4 will not extend through the outer weld 6.

However, if the product to be contained in the device is a thin product or has low viscosity, the product may flow around the edge of the bottom layer 4. This is indicated by an arrow in FIG. 2, and further inside between the bottom layer 4 and the pocket layer 5, whereby the users hand will be soiled.

Figure 3A:
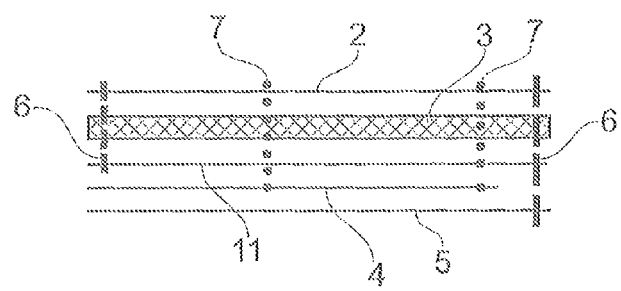
FIG. 3 illustrates one embodiment of the device according to the present invention.
Figure 3B:
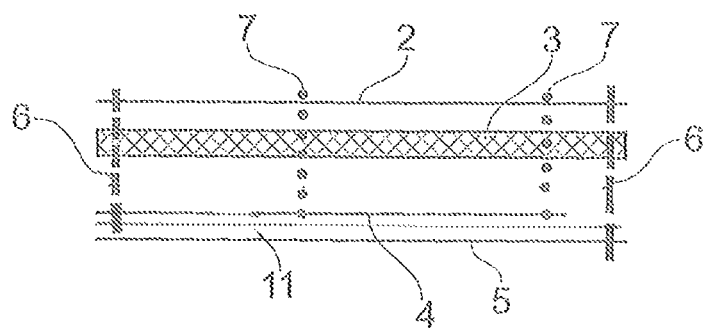

This "leakage" can be prevented by arranging an additional layer 11 between the bottom layer 4 and the storage layer 3, as can be seen in FIG. 3. The additional layer 11, which is a thin, elastic film, can be integrated to be part of the storage layer 3, or alternatively part of the bottom layer 4.

The additional layer 11 may also be arranged between the bottom layer 4 and the top layer 5.

By manufacturing the device according to the present invention with an additional layer 11, the product contained in the device will not be able to flow over and around the cut edges of the bottom layer 4, and the users hand will therefore not be soiled.

Figure 4:
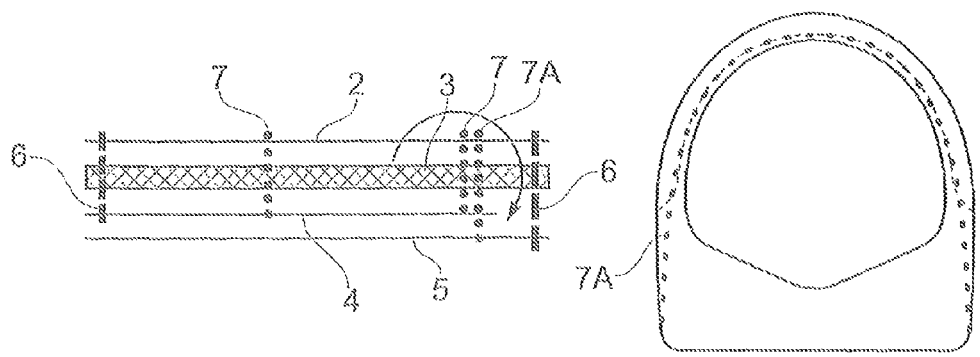
FIG. 4 illustrates a further embodiment of the device according to the present invention.

In FIG. 4 another embodiment of the present invention is shown, where the additional layer 11 is omitted from the device. Here the pocket layer 5 is instead connected to the bottom layer 4, storage layer 3 and the contact layer 2, in order to form the pocket. The pocket layer 5, bottom layer 4, storage layer and the contact layer 2 are then welded, glued etc., where this "weld" 7A then will be placed on or just outside the weld 7 of the storage chamber 10, but inside the bottom layer 4. This will result in that the pocket in this embodiment of the present invention will be somewhat smaller.

How this "weld" is arranged, can be seen at the right side of the FIG. 4, where the "weld" 7A is indicated.

Due to the construction of the device according to the present invention, the device will also during use have a tendency to form an upstanding edge in the area where the part 9 is cut when the user puts his or hers fingers in the pocket. This is a result of the relatively stiff top layer 1 having been removed and part 9 of the bottom layer 4 cut away.

The invention claimed is:

1. Applicator device containing a product, the device comprising an impermeable top layer (1) and an impermeable bottom layer (4), between which two layers (1, 4) at least one intermediate layer is arranged, where the bottom layer (4), the at least one intermediate layer and top layer (1) are connected to each other around their outer peripheries, the bottom layer (4), the at least one intermediate layer and top layer (1) further being connected to each other on an inside of their outer peripheries to form a sealed storage chamber (10) for the product, wherein at least a part (9) of the bottom layer (4) outside and around the sealed storage chamber (10) is cut or cut off (8), and wherein the bottom layer (4) is manufactured from a material less flexible than rest of the layers.

2. Device according to claim 1, characterized in that a pocket layer (5) over a part of its outer edges is connected to the other layers, the pocket layer (5) together with the bottom layer (4) thereby forming an opening for a users hand or finger(s).

3. Device according to claim 2, characterized in that the pocket layer (5) is manufactured from an elastic material.

4. Device according to claim 1, characterized in that an additional layer (11) is arranged either between a storage layer (3) and the bottom layer (4) or between the bottom layer (4) and the pocket layer (5).

5. Device according to claim 4, characterized in that the additional layer (11) is manufactured from a substantially impermeable material.

6. Device according to claim 1, characterized that a storage layer (3) consist of fiber structures in one or more planes, the fiber structures forming cavities containing the product to be applied.

7. Device according to claim 4 or 5, characterized in that the additional layer (11) cover the entire length of the device.

8. Device according to claim 4 or 5, characterized in that the additional layer (1) is constituted of a piece.

9. Device according to claim 1, characterized in that the device further comprises at least a storage layer (3) and a contact layer (2).

\* \* \* \* \*